United States Patent [19]
Yano et al.

[11] Patent Number: 5,547,683
[45] Date of Patent: Aug. 20, 1996

[54] METHOD FOR PRODUCING MICROGRANULATED PARTICLE

[75] Inventors: Yoshiaki Yano, Kakogawa; Tamiji Fujimoto; Takayoshi Hidaka, both of Kobe, all of Japan

[73] Assignee: Kanegafuchi Kagaku Kogyo Kabushiki Kaisha, Osaka, Japan

[21] Appl. No.: 244,375

[22] PCT Filed: Oct. 6, 1993

[86] PCT No.: PCT/JP93/01442

§ 371 Date: Jun. 8, 1994

§ 102(e) Date: Jun. 8, 1994

[87] PCT Pub. No.: WO94/08709

PCT Pub. Date: Apr. 28, 1994

[30] Foreign Application Priority Data

Oct. 9, 1992 [JP] Japan .................. 4-297905

[51] Int. Cl.$^6$ .................. A61K 9/50; B05D 7/02; B32B 5/16
[52] U.S. Cl. .................. 424/501; 424/499; 427/2.15; 427/2.16; 427/2.18; 427/2.19; 427/214; 428/402
[58] Field of Search .................. 424/489, 499, 424/501; 428/402; 427/2.15, 2.16, 2.18, 2.19, 214; 71/64.02, 64.03, 64.5

[56] References Cited

FOREIGN PATENT DOCUMENTS

| | | |
|---|---|---|
| 49-46585 | 5/1974 | Japan . |
| 54-32176 | 3/1979 | Japan . |
| 55-129220 | 10/1980 | Japan . |
| 61-68133 | 4/1986 | Japan . |
| 63-240934 | 10/1988 | Japan . |
| 6-128147 | 10/1994 | Japan . |

OTHER PUBLICATIONS

Y. Fukumori et al., Chem. Pharm. Bull. 39(7) 1806–1812 (1991).

*Primary Examiner*—Carlos Azpuru
*Attorney, Agent, or Firm*—Birch, Stewart, Kolasch & Birch, LLP

[57] ABSTRACT

The present invention relates to a method for producing a microgranulated particle having particle size of not more than 0.2 mm, wherein a fine powder with the average particle size of not more than 10 μm, which is being agitated, tumbled or fluidized, is granulated, with a solution containing a binder alone or a binder and a surfactant being sprayed onto the surface thereof. The present invention allows to produce pharmaceutical preparations for poorly soluble and poorly absorbable drugs and preparations requiring a high content of the active ingredient. Also, it can provide an easy-to-handle powdery microgranulated particle in the field of food and fertilizers.

14 Claims, 9 Drawing Sheets

METHOD FOR PRODUCING MICROGRANULATED PARTICLE

TECHNICAL FIELD

The present invention relates to a method for producing a microgranulated particle. More specifically, it relates to a method for producing a microgranulated particle, which can provide a powdery microgranulated particle, which is suitable for pharmaceutical preparations of poorly soluble or poorly absorbable drugs and pharmaceutical preparations for which the content of the active ingredient should be kept high in the pharmaceutical field; and which is easy-to-handle also in the fields of food and fertilizers.

BACKGROUND ART

Before a pharmaceutical product exerts its pharmacological effects, the active ingredient (drug) in an oral solid pharmaceutical preparation is released from the preparation in the digestive tract, dissolved in humoral fluid and absorbed into circulating blood. Poorly soluble drugs, however, may fail to satisfactorily exhibit the pharmacological effects because they, because of low solubility, are sometimes excreted out of the body before they are completely dissolved. To date various methods have been investigated for improving the solubility of poorly soluble drugs. For example, a poorly soluble drug is co-milled with a β-1,4-glucan powder (Japanese Patent Examined Publication No. 53-22138), a poorly soluble drug is kneaded with a water-soluble polymeric base material (Japanese Patent Laid-Open No. 61-63614) and a poorly soluble drug is adsorbed to and carried by the surface of processed starch (Japanese Patent Laid-Open No. 63-101333).

It has long been known that the absorbability of orally administered poorly soluble drugs, in particular, depends on particle size. In such oral preparations, the active ingredient is released after disintegration of the tablet, coating or capsule, and the smaller the particle of the active ingredient is, the more rapidly the active ingredient can be dissolved and absorbed in the digestive tract after administration. Therefore, it is a common practice to make poorly soluble drugs as fine as possible by pulverizing, etc. To produce such a finely milled active ingredient, however, it is necessary to use a special pulverizing device or to dry the active ingredient after precipitating it in a particularly fine form from a solvent in a special process, where the wetting agent is often used in large excess.

On the other hand, an excessively fine powder has a drawback of being difficult in handling upon preparation, filling and packing because it shows poor fluidity and flying. It is therefore impossible to feed the powder alone into capsules; usually, capsule-filling of the powder is facilitated by adding a fluidizing agent as a secondary ingredient. This can greatly reduce the content of an active ingredient and necessitate relatively high-dose administration because of poor solubility and poor absorbability. In the case of drugs to be given at high doses such as antibiotics, it is required to increase capsule size or to take some capsules at one time, causing inconveniences to the patients upon usage. After finely powdering, pharmaceutical formulation designing by granulation, tableting, etc. is usually conducted. Such process, however, often requires additives to obtain such properties as disintegration of the preparation, and dissolution, dispersion and absorption of the drug, which, in case of drugs requiring high dose administration, can often cause inconveniences to the patients upon usage for the same reason as above.

It is, therefore, desired that the microgranulated pharmaceutical preparations be made with maintaining the content of the active ingredient as high as possible in order to make the above-described properties such as fluidity and flying optimal without sacrificing the advantages of finely powdering such as improvements in solubility and absorbability. However, the attempt to achieve microgranulation only by granulation technology has limits such as a non-uniform particle size distribution. For example, granulation following finely powdering may be achieved by a large number of conventional granulation technologies such as dry coating granulation using a high speed rotary mixer or another apparatus, solid dispersion granulation, fluidized dry granulation, spray drying granulation and wet granulation. However, all these methods provide granulated particles mostly having particle size of not less than 0.2 mm like granules and fine granules. It is technically difficult to prepare a microgranulated particle having particle size of not more than 0.2 mm from a fine powder at high precision and high productivity. Although there are some reports on the obtainment of not more than 0.2 mm fine particles by spray drying granulation or coating on fine core particles, it has not yet been accomplished to obtain a microgranulated particle from a fine powder at high precision only by granulation technology.

As stated above, microgranulation following finely powdering is useful in increasing the rate of absorption of a drug to be given at a high dose. It is expected that the effects of the present art extends beyond the pharmaceutical field because the microgranulation giving particle size of not more than 0.2 mm can be applied also to food and fertilizers.

DISCLOSURE OF INVENTION

The present inventors intensively investigated a method for solving the above-described problems, and found that a microgranulated particle of not more than 0.2 mm with good fluidity and a sharp distribution of particle size can be produced at high productivity by finely pulverizing such a compound as a poorly soluble pharmaceutically effective component together with an appropriate carrier, then by repeating granulation with spraying an aqueous solution of a water-soluble polymer or such an aqueous solution further containing a surfactant as a binder in a gas stream using a means such as a jet nozzle. The inventors also found that granules with the same effects as above can be obtained by additionally performing the process of surface treatment on the surface of the fine powder by mixing and stirring smaller particles such as those of a highly dispersible silica as a fluidizing agent before, during or after granulation process. The inventors made further investigations based on these findings, and developed the present invention.

Specifically, the gist of the present invention relates to:

(1) A method for producing a microgranulated particle with particle size of not more than 0.2 mm, characterized by the step in which a fine powder with the average particle size of not more than 10 μm, which is being agitated, tumbled or fluidized, is granulated with a solution containing a binder or a binder and a surfactant being sprayed onto the surface thereof; and (2) The microgranulated particle with particle size of not more than 0.2 mm, which is produced by the method described in (1) above.

BEST MODE FOR CARRYING OUT THE INVENTION

Figure 1:
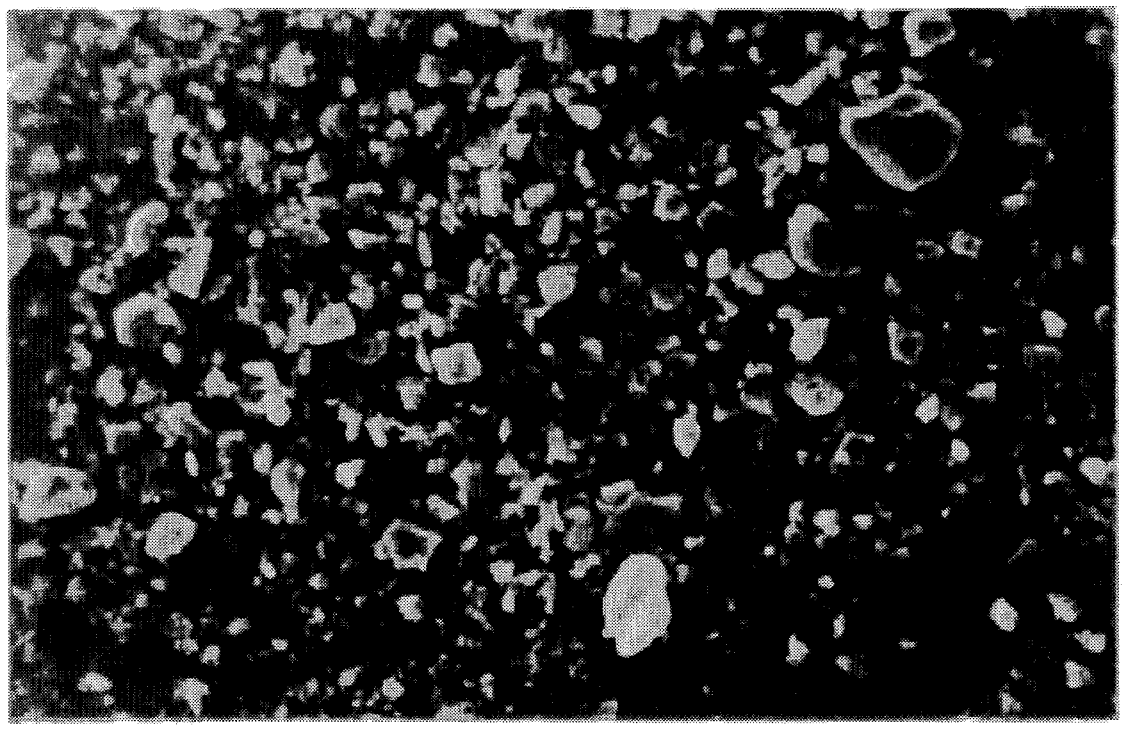
FIG. 1 is a picture showing the particle structure of the pharmaceutical raw material (fine powder), which was observed by scanning electron microscopy (with 500 magnifications.)

In the present invention, a fine powder having the average particle size of not more than 10 μm is usually obtained by pulverizing a given compound along with a carrier. The carrier for obtaining such a fine powder is not subject to limitation; usually, the most effective carrier is selected from the group of talc, calcium hydrogen phosphate, silicic anhydride, crystalline cellulose, lactose, mannitol, etc. As for the apparatus for pulverizing, it is useful to employ such mills as a jet mill and a hammer mill. Using such a mill, the subject compound is finely powdered to particle size of not more than 10 μm. Some starting materials do not need a carrier.

Although the compound to be microgranulated in the present invention, i.e., the compound contained in the fine powder which receives the treatment in the present invention varies depending on the field of application of the present invention without limitation, it is exemplified by poorly soluble and/or poorly absorbable pharmacologically active components in case of pharmaceutical application. Here, any poorly soluble and/or poorly absorbable pharmacologically active component can be used without limitation as to the degree of solubility or absorbability, as long as its low solubility or low absorbability necessitates some pharmaceutical formulation designing. Specifically, the present invention is applicable to any one of the drugs including antibacterial agents, antiviral agents, circulatory drugs, immunoregulators, anticancer agents and anti-inflammatory agents, as long as enhancement of its solubility or absorbability is required because of its low solubility or absorbability. The present invention is also applicable to such fields as food and fertilizers, according to various purposes. In the present specification, as an example of a poorly soluble and poorly absorbable drug, an antibacterial agent referred to as KRM-1648 is exemplified in Examples.

Success in preparing a microgranulated particle depends on how uniformly fine droplets of a binder or those of a binder and surfactant are sprayed and coat the surface of the fine powder to bind the particles with each other. The above-described process is facilitated by mixing and stirring particles which are smaller than the fine powder before, during or after the process in order to improve the surface condition of the fine powder prior to or during granulation. In this case, the binder is preferably a water-soluble polymer, with a greater preference given to a binder having a low molecular weight and low viscosity because it is weak in binding power and provides good properties for microgranulation. In general, a water-soluble polymer increases its viscosity and binding power to form a gel as the molecular weight increases, causing inconveniences in handling, which in turn makes it difficult to obtain a microgranulated particle.

The binder used in the present invention is a water-soluble polymer such as hydroxypropyl cellulose, hydroxypropyl methyl cellulose, sodium carboxymethyl cellulose and polyvinylpyrrolidone. In particular, those of low viscosity as described above are preferred, and those whose binding power is not too high are preferably used, since they permit easy control of granulated particles. Examples of hydroxypropyl cellulose of low viscosity include HPC-SL and HPC-SSL, both produced by Nippon Soda Co., Ltd., with preference given to the grade of HPC-SSL. As binders, the above-mentioned water-soluble polymers may be used singly or in combination of two or more kinds.

In the present invention, substances other than the above-described water-soluble polymers, such as those commonly used as binders, e.g., starch glue, carmellose, tragacanth, gum arabic and sodium alginate, can also be used for the above-described purpose by appropriately adjusting the amount. The amount of such ordinary binders combinedly used is appropriately adjusted, depending on the apparatus used.

Binders having a high molecular weight are undesirable in terms of its handling, particle properties at the time of granulation (e.g., uniform coating on the particle surface) and other factors because their viscosity is so high that they form a gel due to their strong binding power. However, as a solution to this problem, the viscosity can be reduced by the addition of a surfactant.

When a surfactant is used in combination with a binder, the surfactant is not subject to limitation, as long as its addition can lower the viscosity of binder or improve water wetting during granulation to prevent the formation of "aggregates," with a preference given to hydrophilic surfactants which can offer a greater improvement in water wetting. Examples of preferable surfactants include hydrophilic fatty acid esters of sucrose, polyoxyl stearate, polyethylene glycol, polysorbate and polyoxyethylene polyoxypropylene glycol. These surfactants exert an effect to improve the absorption of poorly soluble drug as well as the above-described effects to lower the viscosity of binder and control granulation.

In the present invention, a fine powder is granulated in the presence of a binder such as a water-soluble polymer or in the presence of such a binder and a surfactant, which is combined with a surface treatment using particles smaller than the fine powder as a fluidizing agent to accomplish microgranulation giving a very uniform particle size distribution. In the granulation which is performed in the presence of a binder like a water-soluble polymer or in the presence of such a binder and a surfactant, as stated above, to the surface of the fine powder being agitated, tumbled or fluidized, a water-soluble polymer alone, in the former case, is sprayed via a nozzle, or a surfactant and a water-soluble polymer, in the latter case, are sprayed via respective nozzles, and a mixture of the both may be sprayed. In this spraying, the amount of surfactant added is normally not more than 10% by weight of the fine powder, and the amount of water-soluble polymer added is normally 1 to 20% by weight of the fine powder.

In the present invention, effective matching of the combination of a fine particle, a hydrophilic surfactant and a binder with the apparatus presumably contributes to the accomplishment of microgranulation.

For the surface treatment performed by mixing and stirring fine particles in the present invention, particles smaller than the fine powder are used, and high speed dry mixing, for example, can be used. In the present invention, by mixing and stirring such fine particles, they are made to adhere to the surface of the fine powder or made to be co-present in the vicinity of the surface. In the present invention, it is referred to as surface treatment to make the surface of the fine powder or the vicinity of the surface thereof have fine particles.

Preferable fine particles are those of a highly dispersible silica of light silicic anhydride (Aerosil, produced by Japan Aerosil Industry Co., Ltd.). For example, Aerosil #200 (produced by Japan Aerosil Industry Co., Ltd.) is a product of particles having the specific surface area of 200 $m^2/g$ and the average particle size of 12 nm. The surface treatment with a fine particle is performed before, during or after the granulation process. The surface treatment with a fine particle may be conducted at any time and at any frequency without limitation, before, during or after the above-described granulation process. For example, the surface treatment and the granulation process may be alternatively repeated. In such case, the frequency of the repeat is appropriately chosen, depending on the kinds and amounts of the fine powder, binder, surfactant, etc., and the desired particle size of the granulated particle. This alternative repeating method is preferable because it offers uniform coating and yields a heavy granulated particle. In the present invention, by combining the surface treatment using a fine particle and the granulation process, positive effects are obtained on the granulated particle itself and in improving the fluidity of the microgranulated particle obtained by the granulation. The amount of the fine particle used for this purpose is normally 1 to 5% by weight of the fine powder.

In the present invention, other components such as an absorption promoter and a stabilizer can also be used in the above-described method. These other components are optionally chosen without limitation, depending on the compound to be granulated. For example, when the subject compound is a water-soluble but poorly absorbable peptide, an absorption promoter may be used concurrently. The usage of these other components may be optionally determined without limitation, and they can be added at the time of co-pulverizing the subject compound and a carrier or at the time of the surface treatment using a fine particle, or at the time of granulation in the presence of a surfactant and a binder like a water-soluble polymer.

An apparatus usable for both the process of mixing and stirring a fine particle and the process of microgranulation in the present invention should have multiple functions as described below, in addition to an ordinary function of fluidized bed granulation coating. An example is Wurster fluidized bed granulation coaters (e.g., those produced by Glatt K.K. or Powrex Corporation). This apparatus, which has a cylindrical Wurster column set at the center of a container, can fluidize a fine powder or a granulated particle through the column in a single direction by an upward gas stream (jet stream), spray fine droplets of a binder or those of a binder and a surfactant to the subject particle from the jet nozzle at the bottom for coating (bottom spray method) and perform granulation and drying.

In addition to the above-described apparatus, multi-function combined granulation coaters of the agitating tumbling fluidized bed type (e.g., SPIR-A-FLOW granulation coater, produced by Freund Industrial Co., Ltd., and New-Marumerizer, produced by Fuji Paudal Co., Ltd.), multi-function combined granulation coaters of the tumbling fluidized bed type (e.g., Multiplex, produced by Powrex Corporation) and other apparatuses can also be used. Spraying methods of these multi-function combined granulation coaters include the top spraying method, in which droplets are sprayed from the top, the middle spraying (tangential spraying) method, in which droplets are sprayed from a side of the bottom, and the bottom spraying method. However, the middle spraying (tangential spraying) method or the bottom spraying method is effective for microgranulation in many cases. In short, it is necessary to control the granulation to yield a microgranulated particle by binding together uniformly coated particles, which can be accomplished by preventing flocking (aggregation) of the subject particles during the granulation process by minimizing the diameter of the droplets of a binder and a surfactant and increasing the speed at which the droplets collide with the fine powder or granulated particle during spraying and granulation. Such apparatus with multiple functions is exemplified by the one using one of the above-described spraying methods. The concentration/amount of the fine particle, hydrophilic surfactant, binder, etc. used for such surface treatment and granulation are optionally chosen according to the apparatus used so that the granulated particle has desired particle size of not more than 0.2 mm. The particle size mentioned here is the measurements obtained by scanning electron microscopy or by sieving.

The granulated particle thus obtained has particle size of not more than 0.2 mm, preferably not more than 0.1 mm, very sharp particle size distribution, improved fluidity and improved water wetting. The granulated particle of the present invention is also useful as a dosage form for pharmaceutical preparations requiring high dose administration because they have a high content of the active ingredient because of excipient-free granulation. Also, improvement in absorption can be expected. Usually, the obtained granulated particle contains a fine powder at not less than 80% and an active ingredient at not less than 60%, preferably not less than 70%. Of course, this granulated particle can be tableted by ordinary methods. They are also applicable to such fields as food and fertilizers as well as pharmaceuticals.

The present invention is hereinafter described in more detail by means of the following working examples and test examples, but the invention is not limited by these examples.

In the examples of the present invention, KRM-1648 ($C_{51}H_{64}N_4O_{13}$, M.W.=941.09), a drug under research and development by Kanegafuchi Kagaku Kogyo K.K., was used as a poorly soluble and poorly absorbable drug model. KRM-1648 is a poorly soluble antibacterial substance which hardly dissolves in water. Because it has a dark purple color, particularly when it is finely powdered, poses problems in handling during preparation as described above, including contamination and flying. KRM-1648 is an abbreviation for 3'-hydroxy-5'-[4-isobutyl-1-piperazinyl]benzoxazinorifamycin, a derivative of rifamycin S, exhibiting strong antibacterial action against infectious atypical acid-fast bacteria such as *Mycobacterium avium* complex and *Mycobacterium tuberculosis* to prevent opportunistic infection in persons with immunological depression.

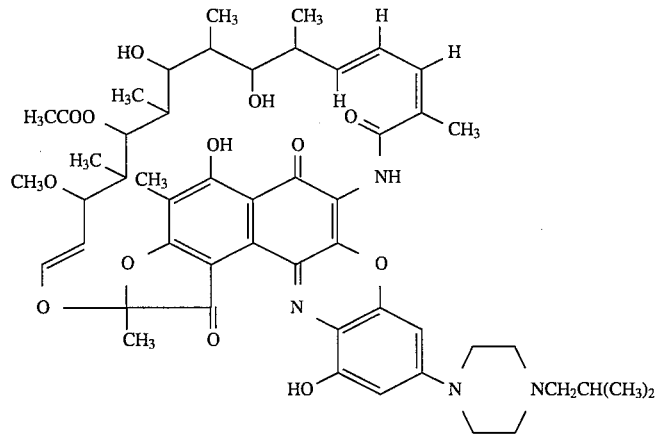

EXAMPLE 1

Crystalline KRM-1648 having the average particle size of about 20 to 40 μm, mixed with JP D-mannitol (produced by Kao Corporation) as a carrier in a 4:1 ratio by weight, was twice pulverized using a hammer mill (Sample Mill KIIW-1, produced by Fuji Paudal Co., Ltd.) to yield a fine powder of not more than 10 μm in the average particle size, which was used as a starting material for preparation. 250 g of this fine powder and 5 g of Aerosil #200 (produced by Japan Aerosil Industry Co., Ltd.) were placed in a Wurster fluidized bed granulation coater (Glatt GPCG-1 Wurster, produced by Glatt K.K.) and stirred and mixed at a high speed in the fluidized bed chamber so that the Aerosil #200 adheres to the surface of the starting material powder for surface treatment. Then, an aqueous mixture solution containing 0.05% of DK Ester F-160 (produced by Dai-ichi Kogyo Seiyaku Co., Ltd.), a fatty acid ester of sucrose, and 5% of HPC-SSL (produced by Nippon Soda Co., Ltd.), a water-soluble polymer hydroxypropyl cellulose, was sprayed in the form of gas stream via a jet nozzle using a bottom spray for granulation. When granulation with spraying was carried out until the ratio of HPC-SSL to the active ingredient, KRM-1648, became 5%, spraying was stopped, and 4 g of the above-described Aerosil #200 was added, and the particle was subjected to surface treatment in the drying process by high speed fluidized stirring and mixing within the same apparatus, to yield a fine and half-granulated particle having particle size of not more than about 20 μm as determined by scanning electron microscopy.

EXAMPLE 3

The fine and half-granulated particle obtained in Example 1 was placed in a Wurster fluidized bed granulation coater (Glatt GPCG-1 Wurster, produced by Glatt K.K.), and then the above-described aqueous solution containing 0.05% of DK Ester F-160 (produced by Dai-ichi Kogyo Seiyaku Co., Ltd.), a fatty acid ester of sucrose, and 5% of HPC-SSL (produced by Nippon Soda Co., Ltd.,) a water-soluble polymer hydroxypropyl cellulose, was sprayed in the form of gas stream via a jet nozzle during granulation until the ratio of HPC-SSL to the active ingredient KRM-1648 became 10%. Then, in the drying process, 2 g of Aerosil #200 (produced by Japan Aerosil Industry Co., Ltd.) was added, and the particle was subjected to surface treatment by high speed fluidized stirring and mixing in the same apparatus to yield a microgranulated particle (particle size of 20 to 40 μm as determined by scanning electron microscopy.) The contents of the fine powder and KRM-1648 in the granulated particle were 87% and 70%, respectively.

EXAMPLE 3

The microgranulated particle obtained in Example 2 was placed in a Wurster fluidized bed granulation coater (Glatt GPCG-1 Wurster, produced by Glatt K.K.), and then the above-described aqueous solution containing 0.05% of DK Ester F-160 (produced by Dai-ichi Kogyo Seiyaku Co., Ltd.), a fatty acid ester of sucrose, and 5% of HPC-SSL (produced by Nippon Soda Co., Ltd.), a water-soluble polymer hydroxypropyl cellulose, was sprayed in the form of gas stream via a jet nozzle during granulation until the ratio of HPC-SSL to the active ingredient KRM-1648 became 15%. Then, in the drying process, 4 g of Aerosil #200 (produced by Japan Aerosil Industry Co., Ltd.) was added, and the particle was subjected to surface treatment by high speed fluidized stirring and mixing in the same apparatus to yield a microgranulated particle (particle size of 50 to 70 μm as determined by scanning electron microscopy.) The contents of the fine powder and KRM-1648 in the granulated particle were 82% and 66%, respectively.

EXAMPLE 4

Crystalline KRM-1648 having the average particle size of about 20 to 40 μm, mixed with JP D-mannitol (produced by Kao Corporation) as a carrier in a 4:1 ratio by weight, was twice milled using a hammer mill (Sample Mill KIIW-1, produced by Fuji Paudal Co., Ltd.) to yield a fine powder of not more than 10 μm in average particle size, which was used as a starting material for pharmaceutical preparation. 800 g of this finely powdered starting material and 16 g of Aerosil #200 (produced by Japan Aerosil Industry Co., Ltd.) were placed in a SPIR-A-FLOW agitating and tumbling fluidized bed granulation coater (produced by Freund Industrial Co., Ltd., SFC-MINI), and stirred and mixed at a high speed in the fluidized bed chamber to give surface treatment with the Aerosil #200 to the surface of the starting material powder. Then, an aqueous solution containing 0.05% of DK Ester F-160 (produced by Dai-ichi Kogyo Seiyaku Co., Ltd.), a fatty acid ester of sucrose, and 5% of HPC-SSL (produced by Nippon Soda Co., Ltd.), a water-soluble polymer hydroxypropyl cellulose, was sprayed in the form of gas stream via a jet nozzle for granulation. During spraying, the bottom plate is rotating and the powder is agitated and tumbled in the bottom. The above-mentioned middle spraying method (tangential spraying) allows the spraying of the solution to be directed toward the center of the powder.

The spraying was stopped when the granulation proceeded to the step where the ratio of HPC-SSL to the active ingredient KRM-1648 became 12.5%; 16 g of the above-described Aerosil #200 was added; and the particle was subjected to surface treatment in the drying process by high speed fluidized stirring and mixing within the same apparatus to yield a microgranulated particle. To make sure, a 150-mesh sieve was used and a microgranulated particle with particle size of not more than about 0.1 mm was obtained in an 80% yield. The contents of the fine powder and KRM-1648 were 86% and 69%, respectively.

Test Example 1

Figure 2:
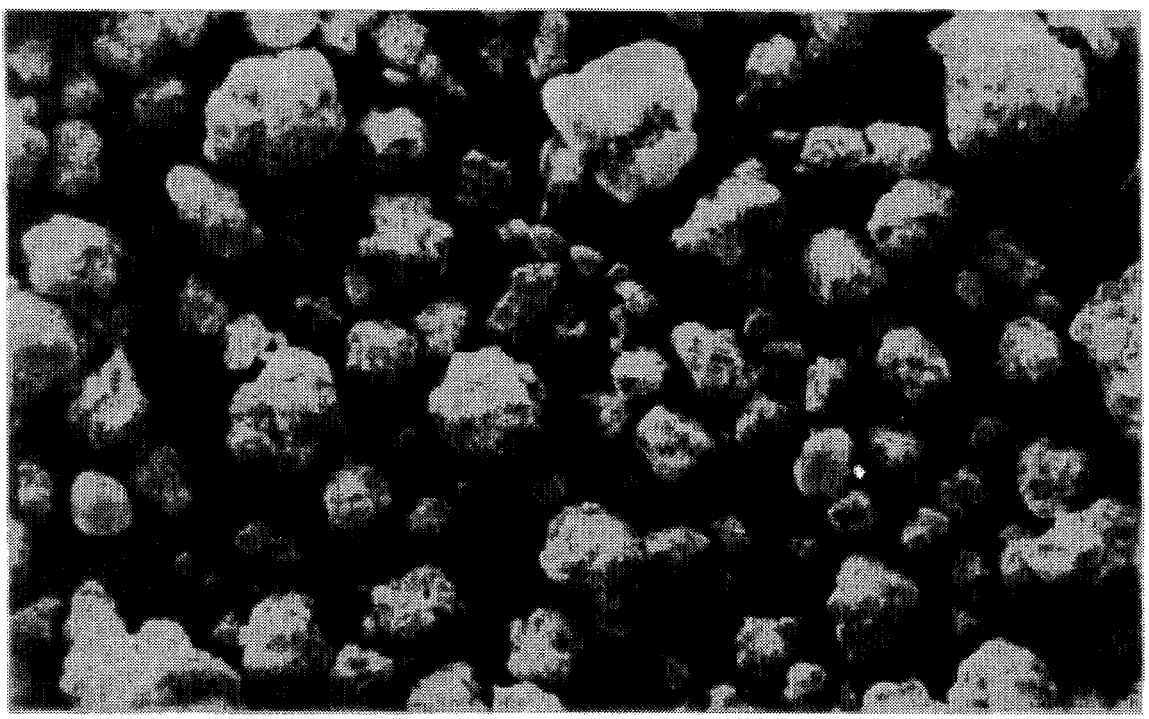
FIG. 2 is a picture showing the particle structure of the microgranulated particle of Example 2, which was observed by scanning electron microscopy (with 500 magnifications.)
Figure 3:
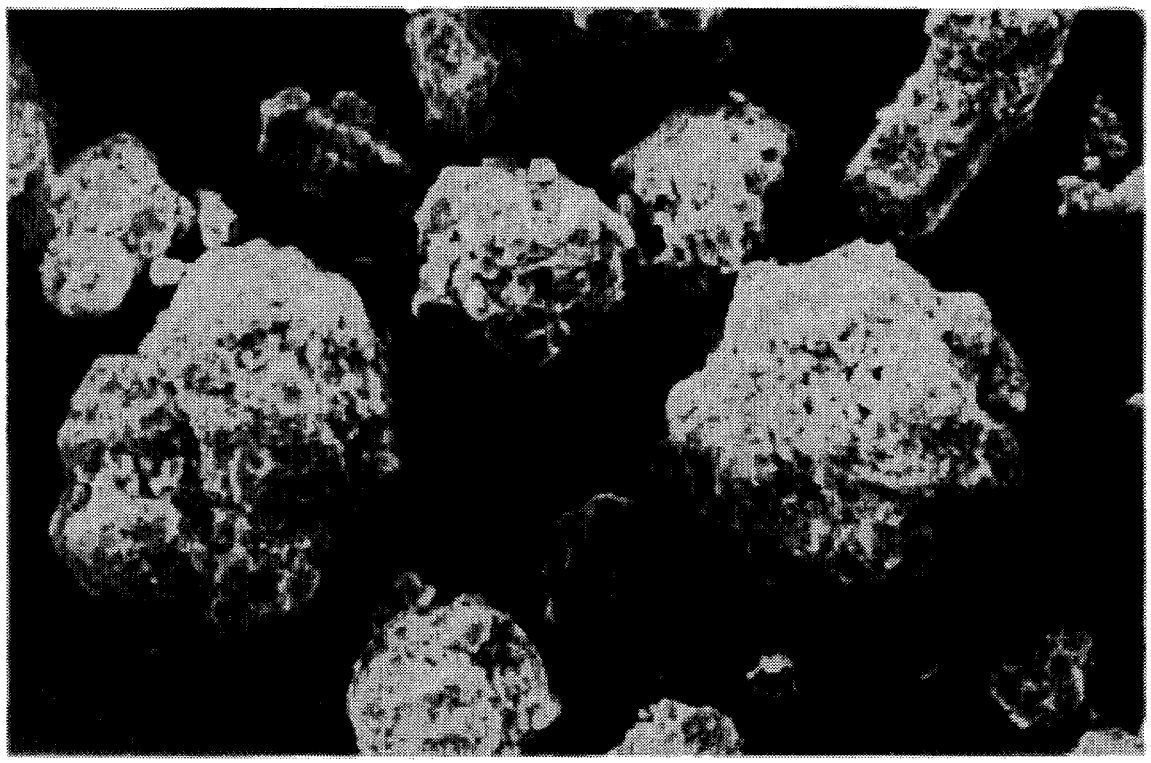
FIG. 3 is a picture showing the particle structure of the microgranulated particle of Example 2, which was observed by scanning electron microscopy (with 1500 magnifications.)
Figure 4:
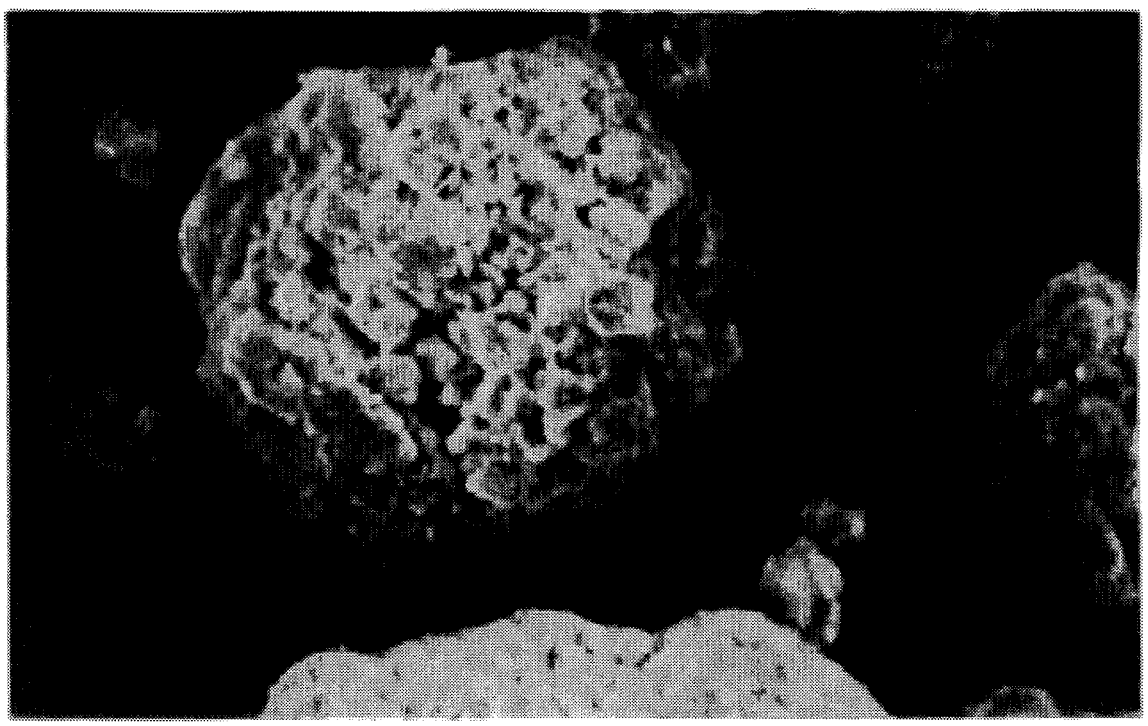
FIG. 4 is a picture showing the particle structure of the microgranulated particle of Example 2, which was observed by scanning electron microscopy (with 3500 magnifications.)
Figure 5:
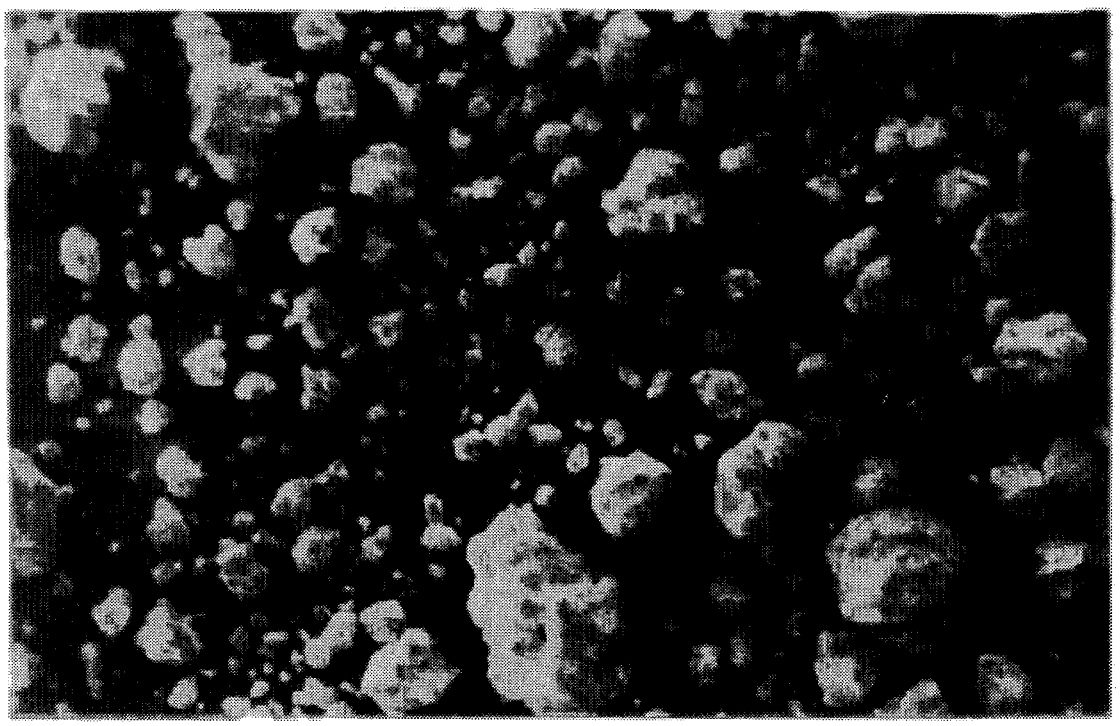
FIG. 5 is a picture showing the particle structure of the microgranulated particle of Example 3, which was observed by scanning electron microscopy (with 100 magnifications.)
Figure 6:
FIG. 6 is a picture showing the particle structure of the microgranulated particle of Example 3, which was observed by scanning electron microscopy (with 500 magnifications.)
Figure 7:
FIG. 7 is a picture showing the particle structure of the microgranulated particle of Example 3, which was observed by scanning electron microscopy (with 2000 magnifications.)

The finely powdered starting material for pharmaceutical preparation obtained by pulverizing, and the microgranulated particles obtained in Examples 2 and 3 were observed by SEM scanning electron microscopy. The apparatus used was of HITACHI S 430 type. The microscopic photo (x 500) of the starting material (fine powder) is given in FIG. 1; those (x 500, x 1500 and x 3500) of the microgranulated particle of Example 2 (hereinafter abbreviated as 10% granulated particle), in FIGS. 2 to 4; and those (x 100, x 500 and x 2000) of the microgranulated particle of Example 3 (hereinafter abbreviated as 15% granulated particle), in FIGS. 5 to 7. As obvious from FIGS. 1 to 7, the particle sizes were about 5 to 10 µm for the starting material, about 20 to 40 µm for the microgranulated particle of Example 2, and about 50 to 70 µm for the microgranulated particle of Example 3.

Figure 8:
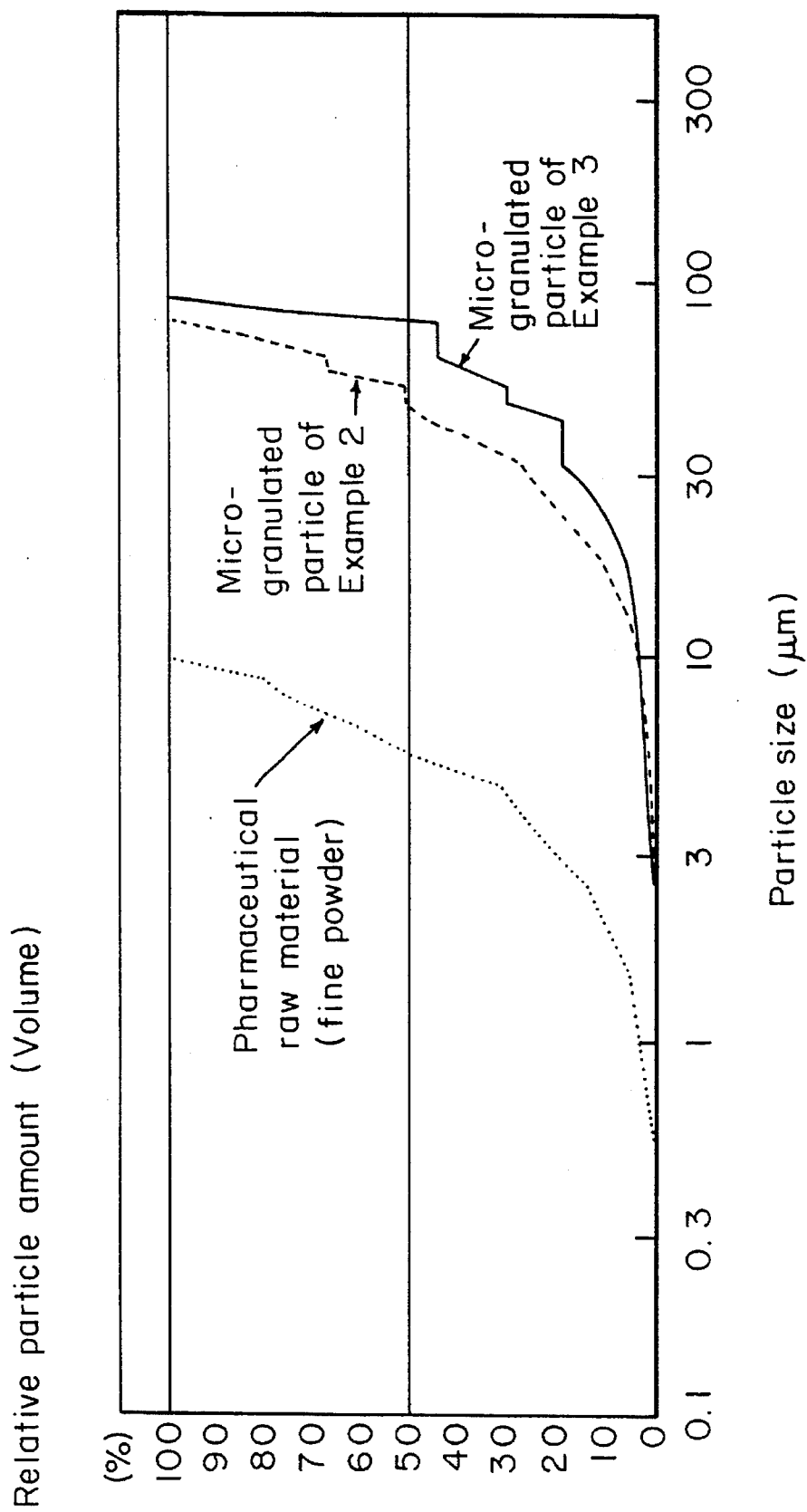
FIG. 8 is a graphic presentation of the particle size distributions of the raw material for pharmaceutical preparation (fine powder), the microgranulated particle of Example 2 (10% granulated product) and the microgranulated particle of Example 3 (15% granulated product).

To accurately grasp the particle size, a volume analysis of the particle size distribution was conducted by image processing after photographing. FIG. 8 shows the results on the particle size distribution based on the particle volume by size. The apparatus used was an image analyzer PIAS III, produced by PIAS Company. As obvious form FIG. 8, it is suggested that the method of the present invention offers a microgranulated particle having particle size of not more than 0.2 mm with the average between 70 and 80 µm and very sharp particle size distribution.

Test Example 2

The finely powdered starting material obtained by pulverizing and the microgranulated particles obtained in Examples 1 through 3 were measured for the angle of repose, an index of fluidity, using a repose angle meter (produced by Konishi Iryoki K.K.). The results, given in Table 1, suggest the fluidity of the granules of the present invention is improved.

TABLE 1

| Samples | Angle of repose |
|---|---|
| Starting material (fine powder) | not less than 55° |
| Microgranulated particle of Example 1 | " |
| Microgranulated particle of Example 2 | 43° |
| Microgranulated particle of Example 3 | 37° |

Test Example 3

Figure 9:
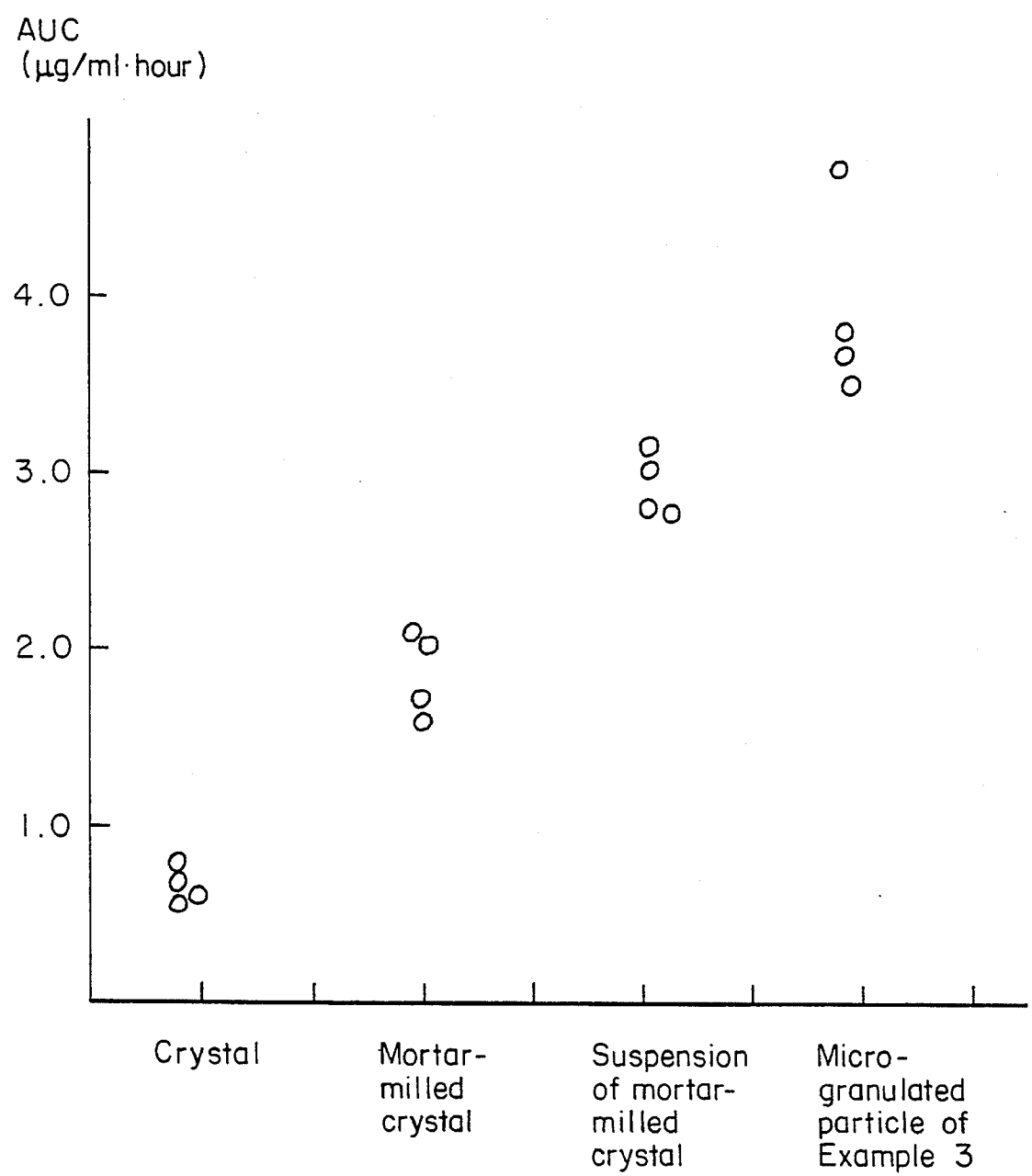
FIG. 9 is a graphic presentation of the comparison of the area under the curve of blood concentration (AUC) in beagles obtained after administration of the microgranulated particle of Example 3 and those obtained after administration of various controls.

To evaluate the absorbability of microgranulated particle (15% granulated particle) obtained in Example 3, the particle was encapsuled in a hard capsule and orally administered to 4 male beagle dogs weighing about 10 kg at a dose of 50 mg KRM-1648/animal. At 1, 3, 5, 8, 12 and 24 hours following administration, the blood concentration was measured by HPLC to obtain the area under the blood concentration curve (AUC). For control, crystalline KRM-1648 before co-pulverizing and a powder obtained by pulverizing the crystal with a mortar, were each encapsuled in hard capsules. These hard capsules, and a suspension of the mortar-milled crystal in 2.5% gum arabic, were each orally administered in the same manner as above, and each AUC was obtained in the same manner for comparison. As obvious from FIG. 9, it was shown that the granulated particle of the present invention have remarkably improved absorbability.

INDUSTRIAL APPLICABILITY

The present invention provides a method for producing a microgranulated particle having markedly uniform particle size of not more than 0.2 mm from a fine powder, which, in the field of pharmaceuticals, allows to produce pharmaceutical preparations of poorly soluble and poorly absorbable drugs and those requiring a high content of the active ingredient. It can provide easy-to-handle materials also in the fields of food and fertilizers.

What is claimed is:

1. A method for producing microgranulated particles, which comprises granulating a fine powder with an average particle size of not more than 10 µm into microgranulated particles having a particle size of not more than 0.2 mm, wherein said fine powder is being agitated, tumbled or fluidized, while spraying a solution containing a binder or a binder and a surfactant onto a surface of the fine powder to coat the fine powder with the binder or the binder and the surfactant.

2. The production method according to claim 1, further comprising in advance of the granulating step, the step of mixing and stirring the fine powder with fine particles having a particle size smaller than the fine powder particle size.

3. The production method according to claim 1, further comprising during and/or after the granulating step, the step of mixing and stirring the fine powder with fine particles having a particle size smaller than the fine powder particle size.

4. The production method according to claim 2, wherein the fine particle is a highly dispersible silica of light silicic anhydride.

5. The production method according to claim 3, wherein the step of mixing and stirring the fine particles and the step of granulating are alternately repeated.

6. The production method according to claim 1, wherein the binder is a low-viscous binder comprising one or more kinds of water-soluble polymers selected from the group consisting of hydroxypropyl cellulose, hydroxypropyl methyl cellulose, sodium carboxymethyl cellulose and polyvinylpyrrolidone.

7. The production method according to claim 1, wherein the surfactant comprises one or more kinds of hydrophilic surfactants selected from the group consisting of hydrophilic fatty acid esters of sucrose, polyoxyl stearate, polyethylene glycol, polysorbate and polyoxyethylene polyoxypropylene glycol.

8. The production method according to claim 1, wherein the fine powder comprises a poorly soluble and/or poorly absorbable pharmacologically active ingredient.

9. The production method according to claim 8, wherein the poorly soluble and/or poorly absorbable pharmacologically active ingredient is an antibacterial agent 3'-hydroxy-5'-(4-isobutyl-1-piperazinyl)-benzoxazinorifamycin.

10. The production method according to claim 1, wherein the content of the fine powder in the granulated particle is not less than 80%.

11. The production method according to claim 1, wherein the granulating step is conducted by using a Wurster fluidized bed granulation coater, or a multi-function combined granulation coater of the agitating and tumbling fluidized bed type or of the tumbling fluidized bed type.

12. A microgranulated particle with particle size of not more than 0.2 mm produced by the method according to claim 1.

13. A pharmaceutical preparation comprising the granulated particle of claim 12, wherein the poorly soluble and/or poorly absorbable pharmaceutically active ingredient is the antibacterial agent 3'-hydroxy-5'-(4-isobutyl-1 -piperazinyl)-benzoxazinorifamycin.

14. The production method according to claim 1, wherein the microgranulated particles have a particle size of not more than 0.1 mm.

* * * * *